United States Patent [19]

Schumacher

[11] 3,979,467
[45] Sept. 7, 1976

[54] PROCESS FOR THE NITRATION OF HALOAROMATICS

[75] Inventor: Ignatius Schumacher, St. Louis, Mo.

[73] Assignee: Monsanto Company, St. Louis, Mo.

[22] Filed: May 9, 1973

[21] Appl. No.: 358,566

[52] U.S. Cl. .................................. 260/646; 260/688
[51] Int. Cl.² .......................................... C07C 79/12
[58] Field of Search ................................... 260/646

[56] References Cited
UNITED STATES PATENTS
3,140,319  7/1964  Sparks ............................... 260/646

Primary Examiner—Leland A. Sebastian
Attorney, Agent, or Firm—J. E. Maurer; N. E. Willis; F. D. Shearin

[57] ABSTRACT

A process for the nitration of halogenated aromatic compounds is improved by carrying out the nitration in the presence of a phosphorus compound in an amount sufficient to produce an ortho-directing effect. Phosphoric acid is particularly effective over a wide range of temperatures.

8 Claims, No Drawings

PROCESS FOR THE NITRATION OF HALOAROMATICS

BACKGROUND OF THE INVENTION FIELD OF THE INVENTION

This invention relates to an improved process for the nitration of halogenated aromatic compounds whereby the ortho to para isomer distribution is increased.

Nitrochlorobenzenes are valuable chemical intermediates in the synthesis of dyes, photographic developers, anti-oxidants and gum inhibitors. Millions of pounds are produced each year to satisfy these needs.

The present methods used in the nitration of halogenated aromatics, for example the nitration of monochlorobenzene, yield a mixture of the para- and ortho-isomers, and place great emphasis on obtaining the para-isomer since it has, in the past, been in greater demand in the market.

The prior art discloses a number of processes for the nitration of aromatic compounds, but these processes are generally directed toward achieving a para-directive effect. As an example, U.S. Pat. No. 3,077,502 discloses that in the nitration of a halobenzene, a sulfonic acid produces a para-directive effect. Further, U.S. Pat. No. 3,140,319 discloses a method of increasing the amount of para-isomer in a nitrohalobenzene nitration product by nitrating the halobenzene with nitric acid in the presence of sulfuric acid, and purports that phosphoric acid can be used in lieu of sulfuric acid to obtain the same effect.

As can be seen from a review of the prior art, the nitration of chlorobenzene historically was conducted under such conditions to maximize the para-isomer formation. Although the para-isomer of a nitrated haloaromatic is necessary for many industrial purposes, the ortho-isomer is necessary for many other industrial purposes, and market demands for the ortho- and para-isomers have been changing. Flexibility in production is now necessary to meet increasing demands in the marketplace for the ortho-isomer, without a corresponding increase in the production of the para-isomer. The present invention solves this problem of controlling the para- to ortho-isomer distribution without increasing the meta-isomer formation or the formation of dinitrated products.

SUMMARY OF THE INVENTION

It is an object of this invention to provide an improved process for the nitration of halogenated aromatic compounds. It is another object to provide an improved process for the nitration of halobenzenes. It is another object to provide an improved process particularly suitable for controlling the ortho to para isomer distribution in the manufacture of nitrochlorobenzene.

These and other objects are achieved in a process for the preparation of a nitro- and halo-substituted aromatic compound wherein a halogenated aromatic compound is contacted with a nitrating agent, the improvement which comprises carrying out the nitration in the presence of a phosphorus compound.

Broadly described, halogenated aromatic compounds are nitrated, according to the process of this invention, by contacting the halogenated aromatic compound with a nitrating agent at a temperature within the range of from about −30° to about 160°C, in the presence of a phosphorus compound. The para to ortho isomer ratio is controlled by the concentration of phosphorus compound present, and the temperature of the reaction.

The halogenated aromatics which can be employed in the process of this invention include: the monohalobenzenes; such as monochlorobenzene, monobromobenzene, monoiodobenzene and monofluorobenzene; the halonaphthalenes, such as chloronaphthalene, bromonaphthalene, iodonaphthalene and the like; dihalogenated benzenes, such as dichlorobenzene, dibromobenzene, chlorobromobenzene, difluorobenzene and the like. However, it has been found that the process of this invention is particularly efficacious with monochlorobenzene.

Any nitrating agent which is capable of nitrating the nucleus of an aromatic compound can be used in the process of this invention, such as a mixed acid (i.e., a mixture of nitric acid and sulfuric acid), concentrated nitric acid, nitric anhydride, nitrogen tetroxide, ethyl nitrate and the like. Generally, the nitrating agent is employed in stoichiometric quantities, or slightly in excess of the amount required, to effect the mono nitration. Concentrated nitric acid which contains 90 percent or more by weight of $HNO_3$ is a preferred nitrating agent.

The nitration of the halogenated aromatic compounds according to the process of this invention can be carried out in the presence of any number of phosphorus compounds. Suitable phosphorus compounds include: phosphoric acids, such as metaphosphoric acid, orthophosphoric acid, triphosphoric acid, pyrophosphoric acid and the like; phosphorus oxides, such as phosphorus pentoxide and the like; phosphorus halides, such as phosphorus oxychloride, phosphorus pentachloride, phosphorus trichloride, and the like; phosphorus acids, such as orthophosphorous acid, metaphosphorous acid, pyrophosphorous acid and the like; and organophosphorus compounds, such as ethyl phosphate, methyl phosphate and the like. However, phosphoric acids are preferred to produce an ortho-directive effect.

In addition to sulfuric acid which can be used with the phosphorus compound in the process of this invention, sulfonic acids can be used with the phosphorus compounds. By the term "sulfonic acid" is meant any organic sulfonic acid which contains one or more sulfonic acid groups, such as organic monosulfonic acids, organic disulfonic acids, organic trisulfonic acids or other organic polysulfonic acids or mixtures thereof which are at least partially soluble in water. The organic portion of the sulfonic acid can be an aliphatic group such as an alkyl group, a cycloaliphatic group, an aromatic group, or a heterocyclic group. Suitable sulfonic acids include aliphatic sulfonic acids, such as methane sulfonic acid, ethane sulfonic acid, propane sulfonic acid, propane disulfonic acid, dodecane sulfonic acid and the like; aromatic sulfonic acids, such as benzene sulfonic acid, toluene sulfonic acid, benzene disulfonic acid, dodecyl benzene sulfonic acid, 1,5-naphthalene disulfonic acid, and the like; cycloaliphatic sulfonic acids, such as cyclobutane sulfonic acid, cyclopentane sulfonic acid and the like. The aforementioned sulfonic acids may be further substituted by one or more substituents. Typical of such substituents are the halogens such as chlorine, bromine, iodine and fluorine, nitro, carboxy and other non-reactive substituents, such as chloromethane sulfonic acid, chlorobenzene sulfonic acid, dichlorobenzene sulfonic acid and the like.

The effective concentration of the phosphorus compound in the process of this invention can vary in wide ranges depending upon the result desired. As an example, when monochlorobenzene is nitrated at about 80°C. using phosphoric acid in the presence of nitric acid, the para- to ortho isomer ratio is about 1.28:1. However, when monochlorobenzene is nitrated at the same temperature using a mixture of nitric acid and sulfuric acid but without any phosphoric acid, the para to ortho-isomer ratio is about 1.63:1. Using a mixture of 50 mole percent of sulfuric acid and 50 mole percent phosphoric acid at 80°C., the para to ortho isomer ratio is about 1.44:1. Other para to ortho isomer ratios can be achieved by adjusting the ratio of phosphoric acid to sulfuric acid.

The process of this invention is not limited to specific reaction temperatures since the process can be carried out at temperatures of from about −30°C. to temperatures of about 160°C. or higher. A reaction temperature of −30°C. can be maintained, for example, by employing a cooling bath comprising a slurry of solid carbon dioxide in acetone and using chloroform as a reaction diluent. However, those skilled in the art will recognize that the rate of reaction at temperatures of from about −30° to 0°C. will be somewhat slow. The minimum temperature for the process of this invention is therefore that temperature just above that at which no reaction between the nitrating agent and the haloaromatic compound will occur. The maximum temperature is only of economic importance for it is dependent upon economic factors rather than technical factors. For example, monochlorobenzene boils at about 130°C. at sea level, and a pressurized reaction vessel is necessary at temperature above 130°C. Temperatures within the range of from about 25° to about 130°C. are desirably used, while temperatures within the range of from about 50° to about 90°C. are preferred.

The specific reaction temperature used in the process of this invention affects the para to ortho isomer ratio. For example, when monochlorobenzene is nitrated at about 25°C. using a mixture of nitric acid and phosphoric acid, the para to ortho isomer ratio is about 1.6:1; however, when the same reaction is carried out at about 100°C. the para to ortho isomer ratio is about 1.2:1. Thus, it can be seen that the para to ortho isomer ratio can be controlled not only by the concentration of phosphorus compound present in the reaction mixture, but also by the temperature at which the nitration is conducted.

After the nitration reaction is complete, the product can be recovered from the reaction by any method well known to those skilled in the art. For example, the reaction mixture is permitted to settle into two phases, i.e., an organic phase and an acid phase. The organic phase is then separated and the acid is recovered for reuse or is discarded. The specific isomers in the organic phase can be separated by any number of methods well known to those skilled in the art, for example surface crystallization from the melt.

DESCRIPTION OF THE PREFERRED EMBODIMENTS

This invention is further illustrated by, but not limited to, the following examples.

EXAMPLES 1–6

To 118 parts (1.05 mole) of monochlorobenzene, 70 parts (1.0 mole) of 90 percent nitric acid combined with 0.01 to 0.99 mole sulfuric acid and 0.99 to 0.01 mole phosphoric acid is added with vigorous stirring. The temperature is maintained at about 80°C. and the acid is added over a 60 to 90 minute period. After all of the acid has been added, the reaction mixture is maintained at 80°C. for about 60–120 minutes. The resulting mixture is permitted to separate into two phases, and the bottom acid layer is drawn off. The results in Table I indicate the effect of the concentration of sulfuric acid and phosphoric acid on the para to ortho isomer ratio.

TABLE I

| Example | Mole $H_2SO_4$ | Mole $H_3PO_4$ | Isomer Ratio (Para/Ortho) |
|---|---|---|---|
| 1 | 0.01 | 0.99 | 1.30/1 |
| 2 | 0.25 | 0.75 | 1.32/1 |
| 3 | 0.42 | 0.58 | 1.36/1 |
| 4 | 0.50 | 0.50 | 1.44/1 |
| 5 | 0.60 | 0.40 | 1.48/1 |
| 6 | 0.99 | 0.01 | 1.62/1 |

EXAMPLES 7–10

The procedure of Examples 1 through 6 was repeated except that the temperature of the reaction was varied. Using a 0.25 mole percent sulfuric acid and 0.75 mole percent phosphoric acid mixture, the para to ortho isomer ratio that is obtained as a function of temperature is shown in Table II.

TABLE II

| Example | Temperature (°C.) | Isomer Ratio Para/Ortho |
|---|---|---|
| 7 | 45 | 1.43/1 |
| 8 | 55 | 1.39/1 |
| 9 | 80 | 1.32/1 |
| 10 | 125 | 1.30/1 |

EXAMPLES 11–15

The procedure of Examples 7 through 10 was repeated except that two moles of phosphoric acid was used for each mole of nitric acid and each mole of monochlorobenzene. No sulfuric acid was present. The results are presented in Table III.

TABLE III

| Example | Temperature (°C.) | Isomer Ratio Para/Ortho |
|---|---|---|
| 11 | 25 | 1.60/1 |
| 12 | 30 | 1.50/1 |
| 13 | 71 | 1.36/1 |
| 14 | 76 | 1.34/1 |
| 15 | 100 | 1.20/1 |

Although the invention has been described in terms of specified embodiments which are set forth in considerable detail, it should be understood this is by way of illustration only and that the invention is not necessarily limited thereto since alternative embodiments and operating techniques will become apparent to those skilled in the art in view of the disclosure. As an example, the preferred embodiments have been described in terms of batch operations although the invention could be practiced using a continuous process. Accordingly, modifications are contemplated which can be made without departing from the spirit of the described invention.

What is claimed is:

1. In a process for the preparation of a nitro- and halo-substituted aromatic compound wherein a halogenated aromatic compound is contacted with a nitrating agent, the improvement which comprises carrying out the nitration in the presence of a phosphorus compound, the phosphorus compound being present in an amount sufficient to produce an ortho-directive effect.

2. In a process of claim 1 wherein the halogenated aromatic compound is a halobenzene.

3. In a process of claim 2 wherein the halobenzene is monochlorobenzene.

4. In a process of claim 1 wherein the nitration is carried out in the presence of a phosphorus compound selected from the group consisting of phosphoric acids, phosphorous acids and phosphoric acid esters.

5. In a process of claim 1 wherein the phosphorus compound is phosphoric acid.

6. In a process of claim 1 for the nitration of monochlorobenzene wherein monochlorobenzene is contacted with concentrated nitric acid at a temperature within the range of from about 0° to about 130°C., the improvement which comprises carrying out the nitration in the presence of phosphoric acid.

7. In a process of claim 6 wherein the nitration is carried out in the presence of a mixture of phosphoric acid and sulfuric acid.

8. In a process of claim 6 wherein the temperature is in the range of about 50° to about 125°C.

* * * * *